United States Patent
Krichen et al.

(10) Patent No.: US 6,250,309 B1
(45) Date of Patent: Jun. 26, 2001

(54) SYSTEM AND METHOD FOR TRANSFERRING INFORMATION RELATING TO AN IMPLANTABLE MEDICAL DEVICE TO A REMOTE LOCATION

(76) Inventors: Jack P. Krichen, 1450 66$^{th}$ Ave., NE., Fridley, MN (US) 55432; James David Webb, 8138 Ranier La., Maple Grove, MN (US) 55311

(*) Notice: Subject to any disclaimer, the term of this patent is extended or adjusted under 35 U.S.C. 154(b) by 0 days.

(21) Appl. No.: 09/358,081

(22) Filed: Jul. 21, 1999

(51) Int. Cl.$^7$ .................................................. A61B 19/00
(52) U.S. Cl. .............................................. 128/899; 600/300
(58) Field of Search ..................... 128/899, 904; 607/4, 5, 9, 30–32, 59–60; 600/300

(56) References Cited

U.S. PATENT DOCUMENTS 5,791,342 * 8/1998 Woodard ............................ 600/300
5,857,967 * 1/1999 Frid et al. ........................... 600/301
5,870,549 * 2/1999 Bobo, II ............................. 709/206

* cited by examiner

Primary Examiner—John P. Lacyk
(74) Attorney, Agent, or Firm—Girma Wolde-Michael

(57) ABSTRACT

The present invention discloses a method of and a system for transferring information from an implantable medical device to a remote location. The system includes a first extensible mark-up language converter for converting information related to the implantable medical device from an initial format to an extensible mark-up language format. A programmer is electrically connected to the implantable medical device and is capable of temporarily saving selected information related to the implantable medical device and capable of transferring the selected information to a remote location. A second extensible mark-up language converter located at the remote location is connected to the programmer and converts the selected information from the extensible mark-up language format to a final format. The selected information can then be manipulated at the remote location.

56 Claims, 10 Drawing Sheets

SYSTEM AND METHOD FOR TRANSFERRING INFORMATION RELATING TO AN IMPLANTABLE MEDICAL DEVICE TO A REMOTE LOCATION

THE FIELD OF THE INVENTION

The present invention relates generally to a system and method used in conjunction with an implantable medical device. More specifically, the present invention relates to transferring information from an implantable medical device to a remote location.

BACKGROUND OF THE INVENTION

Implantable medical device systems known in the art comprise several components, including an implantable medical device, such as a pacemaker or a defibrillator, pacing and/or sensing leads, and a programmer. The leads connect the implantable medical device to the heart of a patient. An implantable medical device, such as a pacemaker or a defibrillator, commonly stores a variety of different types of diagnostic data which assist a clinician or a physician in evaluating both the operation of the patient's heart and the operation of the implanted medical device. The specific diagnostic data stored by the implantable medical device includes a variety of information, including a real-time event recording of pacing events.

The programmer of the implantable medical device system provides multiple functions, including (a) assessing lead performance during a pacemaker or defibrillator implantation, (b) programming the implantable medical device, and (c) receiving feedback information from the implantable medical device for use by the operator.

An analyzer, which is sometimes a subcomponent of the programmer and sometimes an individual component, is a microprocessor-based component designed to assess the electrical performance of a pacing lead system used in conjunction with an implantable medical device system. The analyzer utilizes the programmer as a control and display platform.

It is desirous to view or store information relating to the implatable medical device system or relating to the specific patient having the implantable medical device therein at a remote location. For example, it is desirous to transfer specific information about the implantable medical device to a remote location such that the information can be stored within a database at the remote location or included within a report generated at the remote location. However, prior art medical device systems retrieve information from a medical device either in a memory dump format which mirrors the format of the device and basically "dumps" the information from the implantable medical device to the programmer, or in a specific format, such as an American Standard Code for Information Interchange (ASCII) format, a waveform format, a numeric format, or a binary format. Information in any of these formats cannot easily be transferred via the Internet and converted into coherent information due to formatting issues. Thus, it is extremely difficult to interpret information in any of these formats at a remote location in order to properly store the information or generate a report based upon the information.

Therefore, there is a need for a system which will permit specific desired information to be transferred to a location remote from the medical device in a format which can easily be interpreted and manipulated. The system should easily allow for interpretation of data from the medical device such that the information can be stored within a database or such that a report can be generated based upon the transferred information.

SUMMARY OF THE INVENTION

The present invention overcomes the disadvantages of the prior art by providing a method of and a system for transferring information from an implantable medical device to a remote location in a form which can be manipulated at the remote location.

The present invention has certain objects. That is, the present invention provides solutions to certain problems existing in the prior art such as: (a) an inability to convert information related to an implantable medical device into a format which can be manipulated at a remote location, the conversion taking place within the implantable medical device; (b) an inability to convert information relating to an implantable medical device into a format which can be manipulated at a remote location, the conversion taking place within a programmer used in conjunction with the implantable medical device; (c) an inability to transfer information from the implantable medical device to a remote location in a format which can be easily manipulated at a remote location; (d) an inability to transfer information relating to an implantable medical device to a remote location such that the information can be stored within a database without requiring a device-specific program to decipher the information at the remote location; and (e) an inability to transfer information related to an implantable medical device to a remote location in a format which can generate a report about the implantable medical device without requiring a device-specific program to decipher the information.

The system and method of the present invention provides certain advantages, including: (a) the ability to convert information related to an implantable medical device into a format which can be manipulated at a remote location, the conversion taking place within the implantable medical device; (b) the ability to convert information relating to an implantable medical device into a format which can be manipulated at a remote location, the conversion taking place within a programmer used in conjunction with the implantable medical device; (c) the ability to transfer information from the implantable medical device to a remote location in a format which can be easily manipulated at a remote location; (d) the ability to transfer information relating to an implantable medical device to a remote location such that the information can be stored within a database without requiring a program to decode the information at the remote location; and (e) the ability to transfer information related to an implantable medical device to a remote location in a format which can generate a report about the implantable medical device without requiring a program to decipher the information.

The system and method of the present invention has certain features, including a first extensible mark-up language (XML) converter for converting information relating to the implantable medical device from an initial format, such as a memory dump format, ASCII format, a waveform format, a numeric format, or a binary format to an XML format. Another feature of the present invention is a second XML converter located at a remote location for converting the selected information from the XML format to a database usable format or a report format. This invention works with standard communications modules, such as a transmission control protocol/internet protocol (TCP/IP) module, located at both the location of the implantable medical device and at the remote location. Thus, a feature of the present invention is the ability to transfer the desired information about the implantable medical device over most communication modules to the remote location via an internet connection such as a local area network connection, a telephone line connection, or a radio frequency connection.

Other objects, advantages, and features of the invention will become apparent by referring to the appended drawings, detailed description, and claims.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
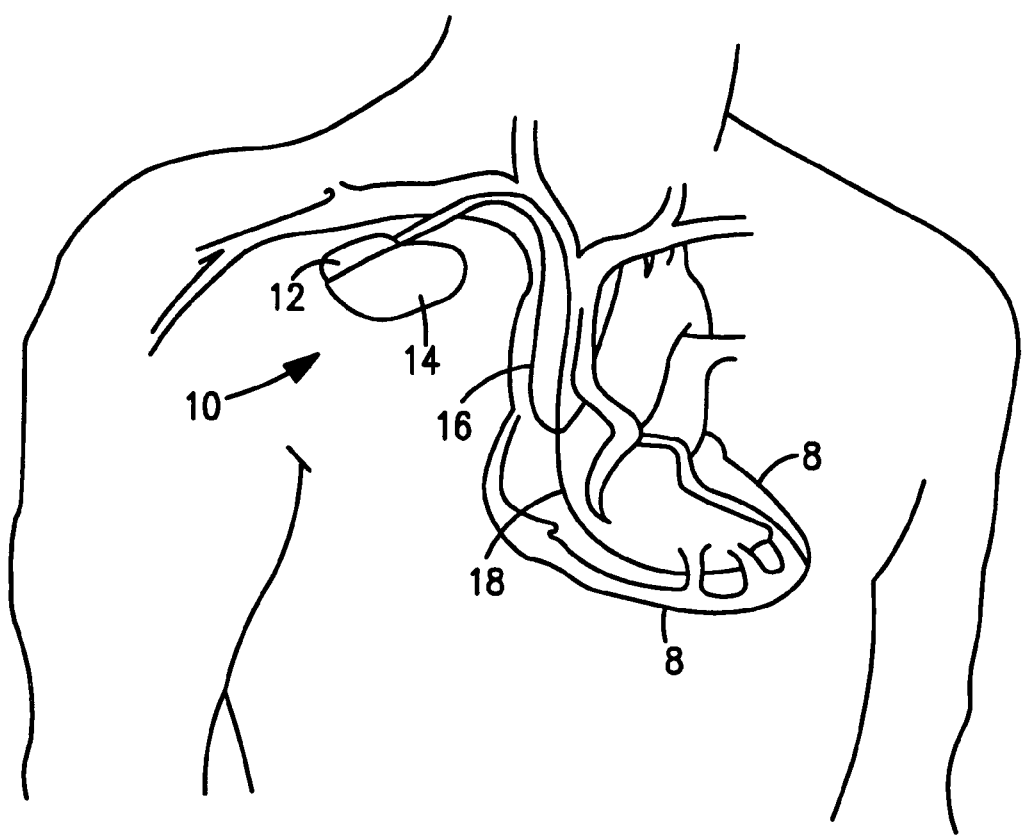
FIG. 1 is a simplified schematic view of one embodiment of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
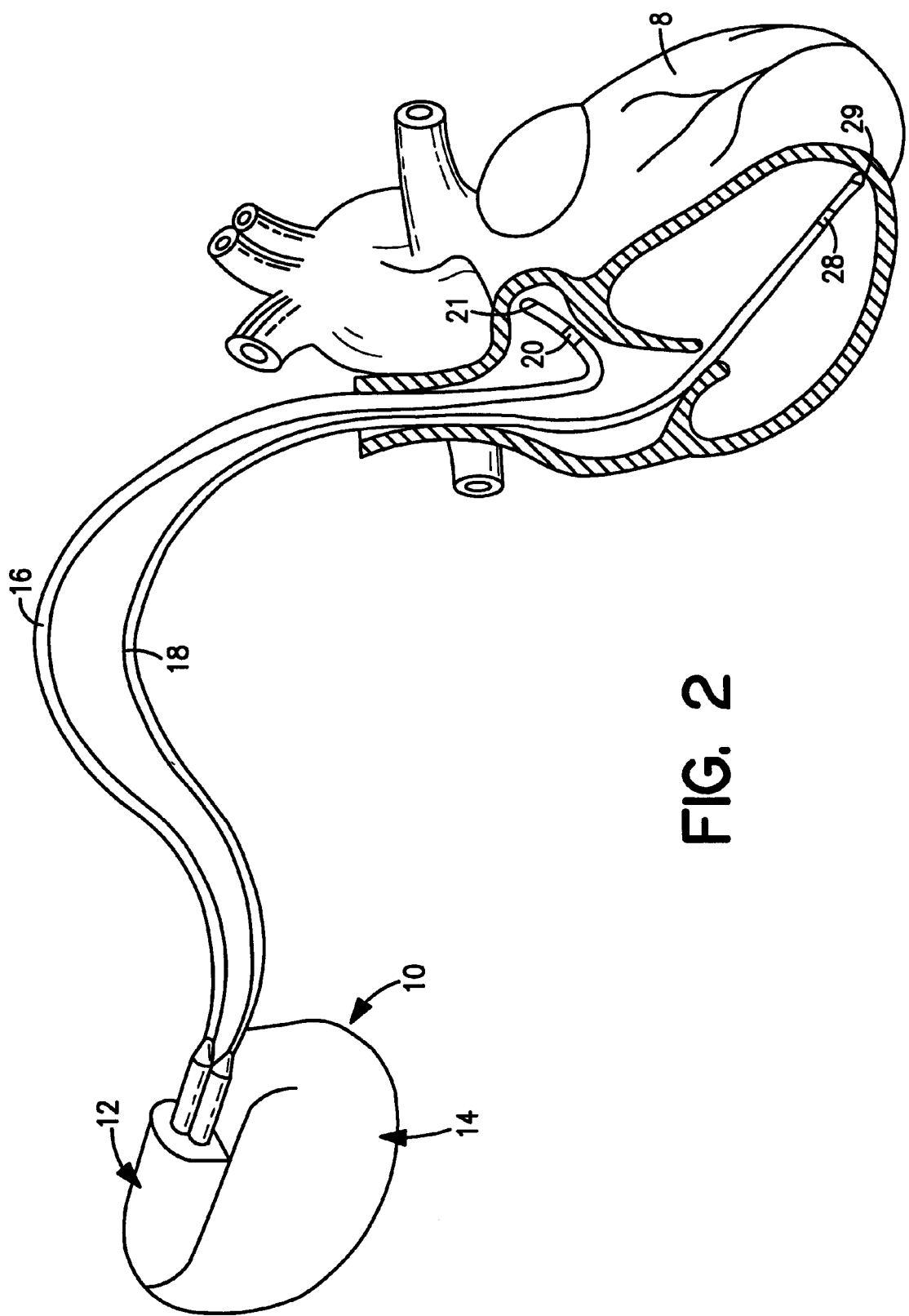
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
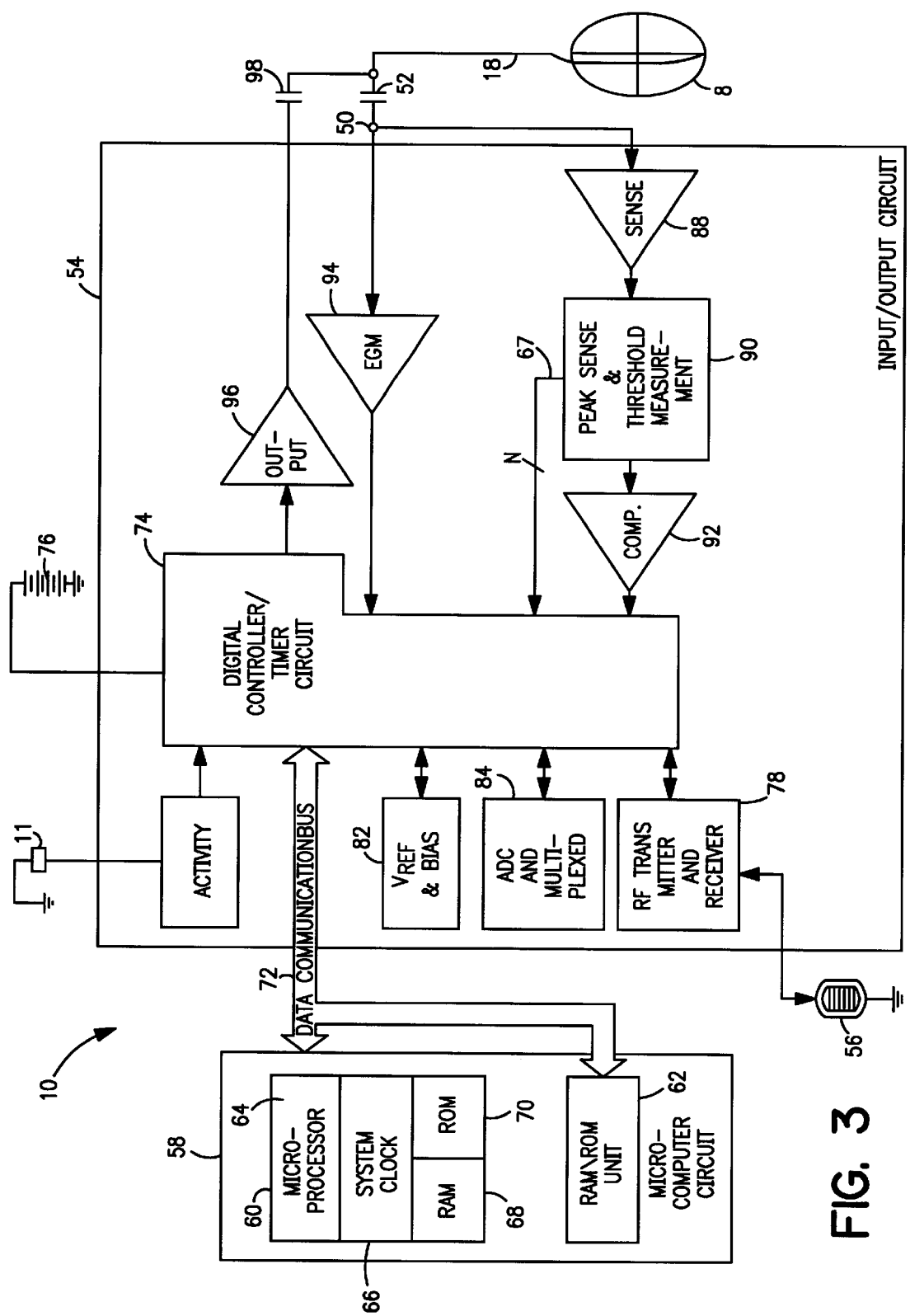
FIG. 3 is a block diagram illustrating the constituent components of an implantable medical device.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However, it is understood that similar circuitry and connections not explicitly shown in FIG. 3 apply to lead 16 (shown in FIGS. 1 and 2).

Figure 6:
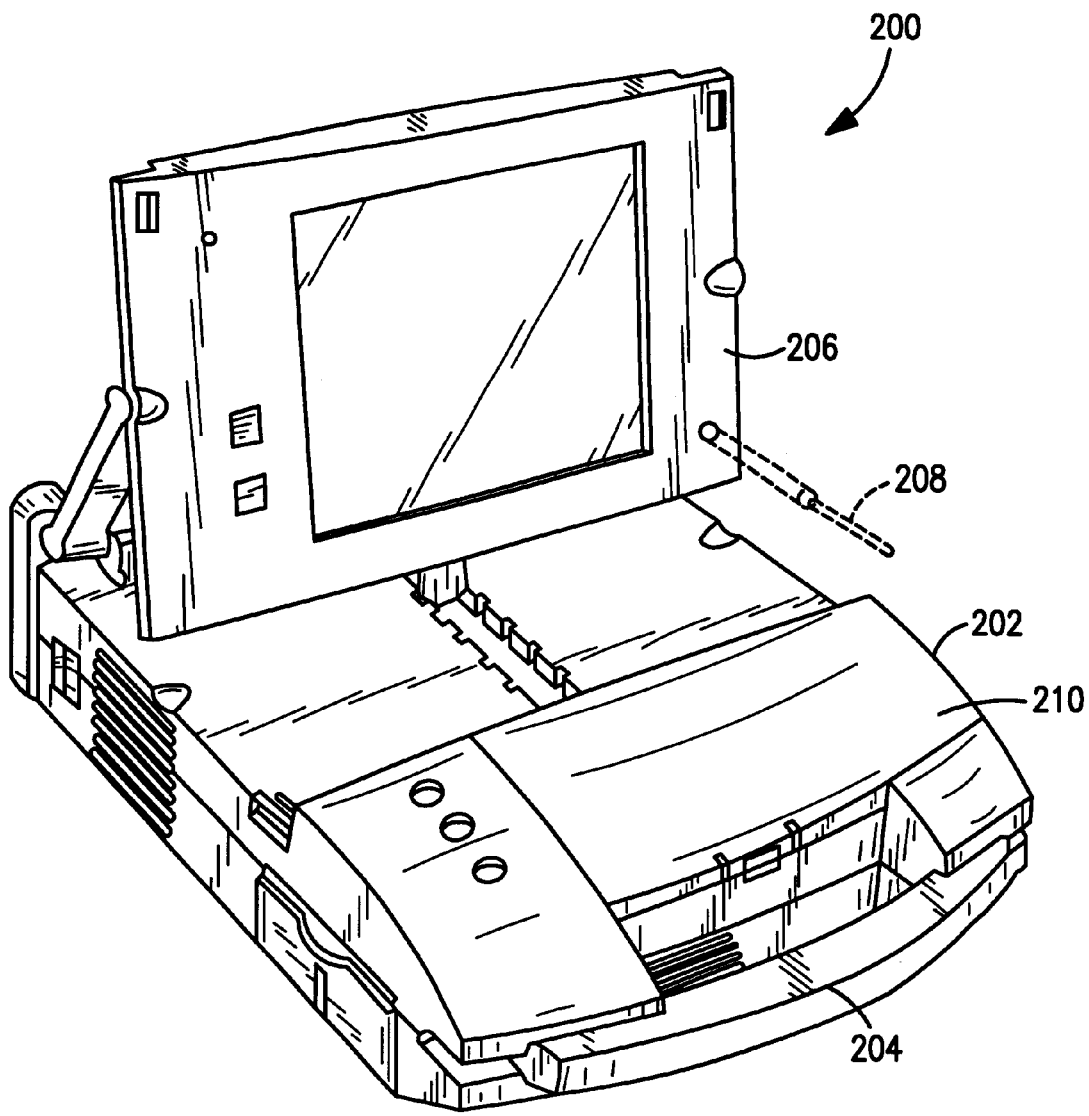
FIG. 6 is a perspective view of a programmer unit used in conjunction with an implantable medical device.

IMD 10 in FIG. 3 is most preferably programmable by means of an external programming unit (shown in FIG. 6). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
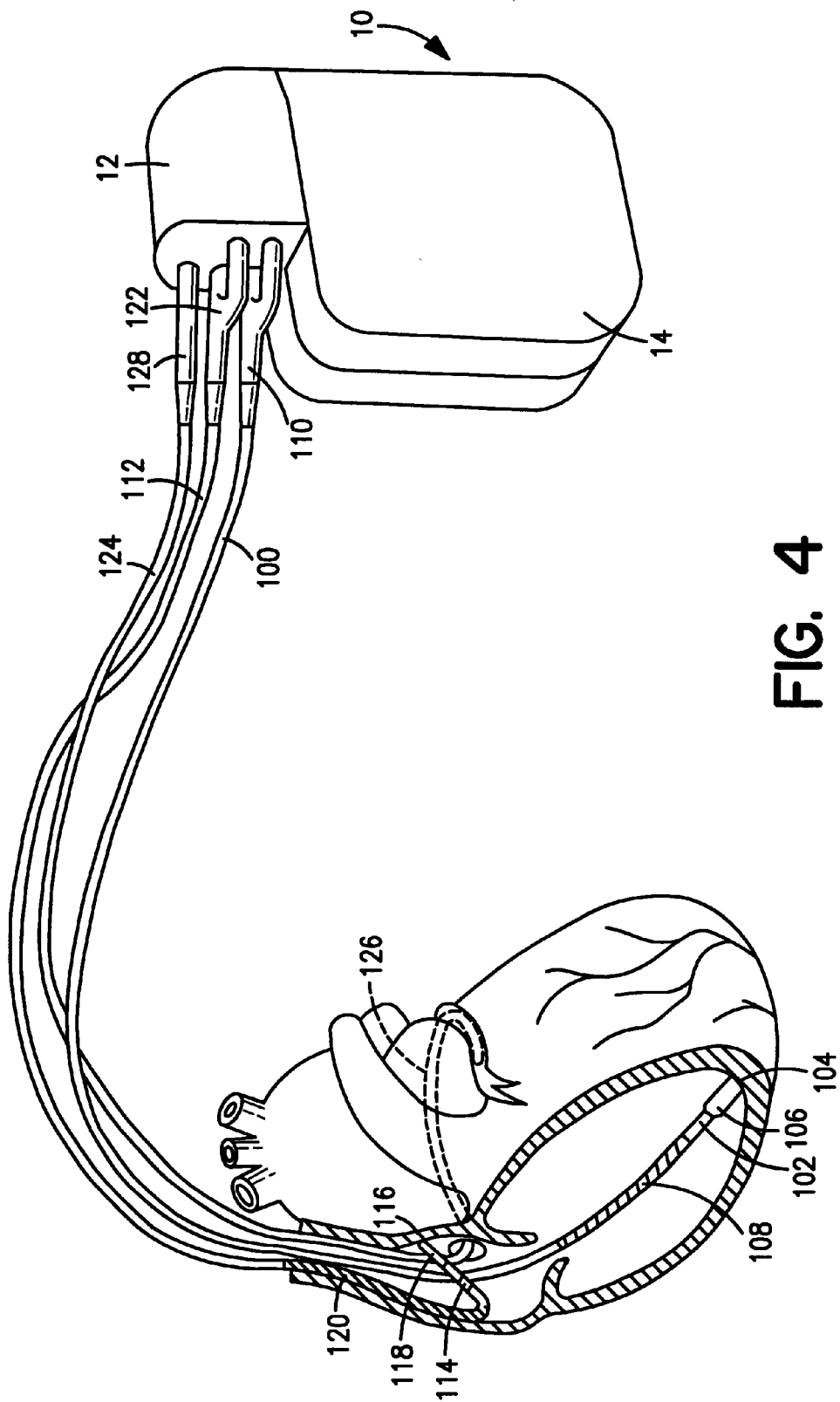
FIG. 4 is a simplified schematic view of an implantable medical device with leads positioned within passageways of a heart.
Figure 5:
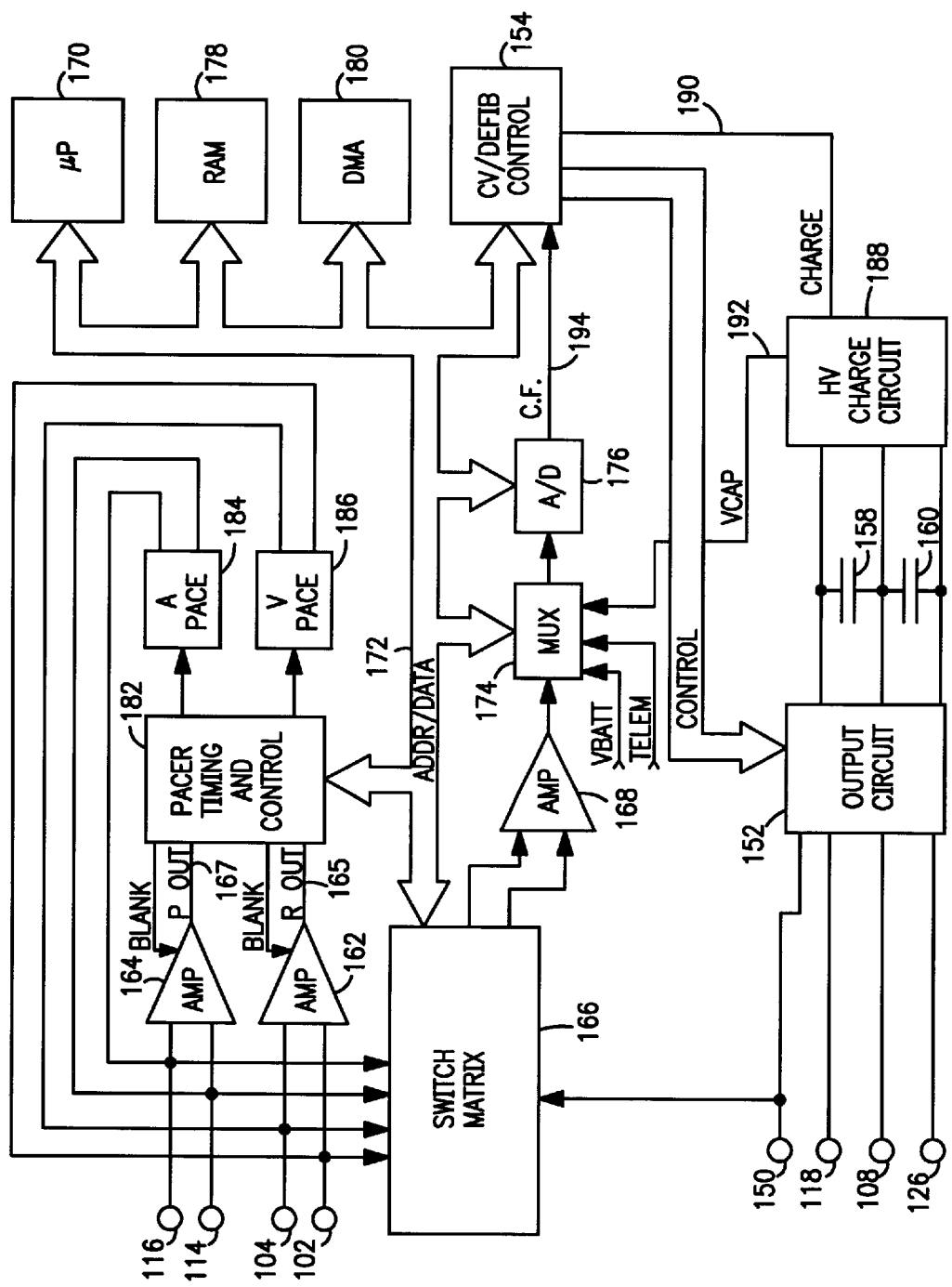
FIG. 5 is a partial block diagram illustrating one embodiment of an implantable medical device used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 100 carrying three concentric coiled conductors separated from one another by tubular insulative sheaths. Located adjacent the distal end of lead 100 are ring electrode 102, extendable helix electrode 104 mounted retractably within insulative electrode head 106 and elongated coil electrode 108. Each of the electrodes is coupled to one of the coiled conductors within lead body 100. Electrodes 102 and 104 are employed for cardiac pacing and for sensing ventricular depolarizations. At the proximal end of the lead is bifurcated connector 110 which carries three electrical connectors, each coupled to one of the coiled conductors. Elongated coil electrode 108, which is a defibrillation electrode 108, may be fabricated from platinum, platinum alloy or other materials known to be usable in implantable defibrillation electrodes and may be about 5 cm in length.

The atrial/SVC lead shown in FIG. 4 includes elongated insulative lead body 112 carrying three concentric coiled conductors separated from one another by tubular insulative sheaths corresponding to the structure of the ventricular lead. Located adjacent the J-shaped distal end of the lead are ring electrode 114 and extendable helix electrode 116 mounted retractably within an insulative electrode head 118. Each of the electrodes is coupled to one of the coiled conductors within lead body 112. Electrodes 114 and 116 are employed for atrial pacing and for sensing atrial depolarizations. Elongated coil electrode 120 is provided proximal to electrode 114 and coupled to the third conductor within lead body 112. Electrode 120 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 122 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 124 carrying one coiled conductor coupled to an elongated coiled defibrillation electrode 126. Electrode 126, illustrated in broken outline in FIG. 4, is located within the coronary sinus and great vein of the heart. At the proximal end of the lead is connector plug 128 carrying an electrical connector coupled to the coiled conductor. Elongated coil defibrillation electrode 126 may be about 5 cm in length.

IMD 10 is shown in FIG. 4 in combination with leads 100, 112 and 124, and lead connector assemblies 110, 122 and 128 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 150 in FIG. 5 includes the uninsulated portion of the housing of IMD 10. Electrodes 108, 118, 126 and 150 are coupled to high voltage output circuit 152, which includes high voltage switches controlled by CV/defib control logic 154 via control bus 156. Switches disposed within circuit 152 determine which electrodes are employed and which electrodes are coupled to the positive and negative terminals of a capacitor bank (which includes capacitors 158 and 160) during delivery of defibrillation pulses.

Electrodes 102 and 104 are located on or in the ventricle of the patient and are coupled to the R-wave amplifier 162, which preferably takes the form of an automatic gain controlled amplifier providing an adjustable sensing threshold as a function of the measured R-wave amplitude. A signal is generated on R-out line 165 whenever the signal sensed between electrodes 102 and 104 exceeds the present sensing threshold.

Electrodes 114 and 116 are located on or in the atrium of the patient and are coupled to the P-wave amplifier 164, which preferably also takes the form of an automatic gain controlled amplifier providing an adjustable sensing threshold as a function of the measured P-wave amplitude. A signal is generated on P-out line 167 whenever the signal sensed between electrodes 114 and 116 exceeds the present sensing threshold. The general operation of R-wave and P-wave amplifiers 162 and 164 may correspond to that disclosed in U.S. Pat. No. 5,117,824 to Keimel et al., hereby incorporated by reference herein in its entirety.

Switch matrix 166 is used to select which of the available electrodes are coupled to wide band (0.5—200 Hz) amplifier 168 for use in digital signal analysis. Selection of electrodes is controlled by microprocessor 170 via data/address bus 172, which selections may be varied as desired. Signals from the electrodes selected for coupling to bandpass amplifier 168 are provided to multiplexer 174, and thereafter converted to multi-bit digital signals by A/D converter 176, for storage in random access memory 178 under control of direct memory access circuit 180. Microprocessor 170 may employ digital signal analysis techniques to characterize the digitized signals stored in random access memory 178 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 182 preferably includes programmable digital counters which control the basic time intervals associated with DDD, VVI, DVI, VDD, AAI, DDI and other modes of single and dual chamber pacing well known to the art. Circuitry 182 also preferably controls escape intervals associated with anti-tachyarrhythmia pacing in both the atrium and the ventricle, employing any anti-tachyarrhythmia pacing therapies known to the art.

Intervals defined by pacing circuitry 182 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 170, in response to stored data in memory 178 and are communicated to pacing circuitry 182 via address/data bus 172. Pacer circuitry 182 also determines the amplitude of the cardiac pacing pulses under control of microprocessor 170.

During pacing, escape interval counters within pacer timing/control circuitry 182 are reset upon sensing of R-waves and P-waves as indicated by a signals on lines 165 and 167, and in accordance with the selected mode of pacing on time-out trigger generation of pacing pulses by pacer output circuitry 184 and 186, which are coupled to electrodes 102, 104, 112 and 116. Escape interval counters are also reset on generation of pacing pulses and thereby control the basic timing of cardiac pacing functions, including anti-tachyarrhythmia pacing. The durations of the intervals defined by escape interval timers are determined by microprocessor 170 via data/address bus 172. The value of the count present in the escape interval counters when reset by sensed R-waves and P-waves may be used to measure the durations of R-R intervals, P-P intervals, P-R intervals and R-P intervals, which measurements are stored in memory 178 and used to detect the presence of tachyarrhythmias.

Microprocessor 170 most preferably operates as an interrupt driven device, and is responsive to interrupts from pacer timing/control circuitry 182 corresponding to the occurrence of sensed P-waves and R-waves and corresponding to the generation of cardiac pacing pulses. Those interrupts are provided via data/address bus 172. Any necessary mathematical calculations to be performed by microprocessor 170 and any updating of the values or intervals controlled by pacer timing/control circuitry 182 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 170 into the pacer timing and control circuitry 182 via data bus 172, to control the operation of the escape interval counters therein and to define refractory periods during which detection of R-waves and P-waves is ineffective to restart the escape interval counters.

Alternatively, circuitry for controlling the timing and generation of anti-tachyarrhythmia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 170 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 170 activates cardioversion/defibrillation control circuitry 154, which initiates charging of high voltage capacitors 158 and 160 via charging circuit 188, under the control of high voltage charging control line 190. The voltage on the high voltage capacitors is monitored via VCAP line 192, which is passed through multiplexer 174 and in response to reaching a predetermined value set by microprocessor 170, results in generation of a logic signal on Cap Full (CF) line 194 to terminate charging. Thereafter, timing of the delivery of the defibrillation or cardioversion pulse is controlled by pacer timing/control circuitry 182. Following delivery of the fibrillation or tachycardia therapy microprocessor 170 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 152 under the control of control circuitry 154 via control bus 156. Output circuit 152 determines whether a monophasic or biphasic pulse is delivered, the polarity of the electrodes and which electrodes are involved in delivery of the pulse. Output circuit 152 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

FIG. 6 is a perspective view of programmer unit 200 used in conjunction with the present invention. Programmer unit 200 has various features, including outer housing 202, carrying handle 204, articulate display screen 206, stylus 208, and analyzer 210.

Display unit 206 is disposed on the upper surface of housing 202. Display screen 206 folds down in a closed position when programmer 200 is not in use, thereby reducing the size of programmer 200 and protecting the display surface of display screen 206 during transportation and storage. In the perspective view of FIG. 6, programmer 200 is shown with articulate display screen 206 having been lifted up into one of a plurality of possible open positions such that the display area is visible to a user situated in front of programmer 200. Display screen 206 is preferably an LCD or electroluminescent type, characterized by being relatively thin as compared to a cathode ray tube display, or the like. Display screen 206 is operatively coupled to computer circuitry disposed within housing 202 and is adapted to provide a visual display of graphics and/or alphanumeric data under control of the computer circuitry.

Display screen 206 is provided with touch-sensitivity capability, such that a user can interact with the internal computer by touching the display area of display screen 206 with stylus 208. It is believed that those of ordinary skill in the computer will be familiar with touch-sensitivity display technology, and the details of implementation of such display will not be described further herein. Display screen 206 is the primary input medium for programmer 200, and therefore preferably has sufficient resolution to support operations including selection, gestures, annotation, and character recognition.

Analyzer 210, which in prior art devices was a separate unit capable of connection to programmer unit 200 only via connecting cables, provides a medium for an operator to run a series of diagnostic tests during an implantation procedure of an IMD, such as IMD 10 previously discussed. For example, a continuous-time waveform or a single complex waveform can be analyzed by analyzer 210 and displayed on display screen 206 from a variety of implanted leads, such as a lead positioned in an atrium or ventricle of heart 8 (shown in FIGS. 1, 2 and 4).

Figure 7:
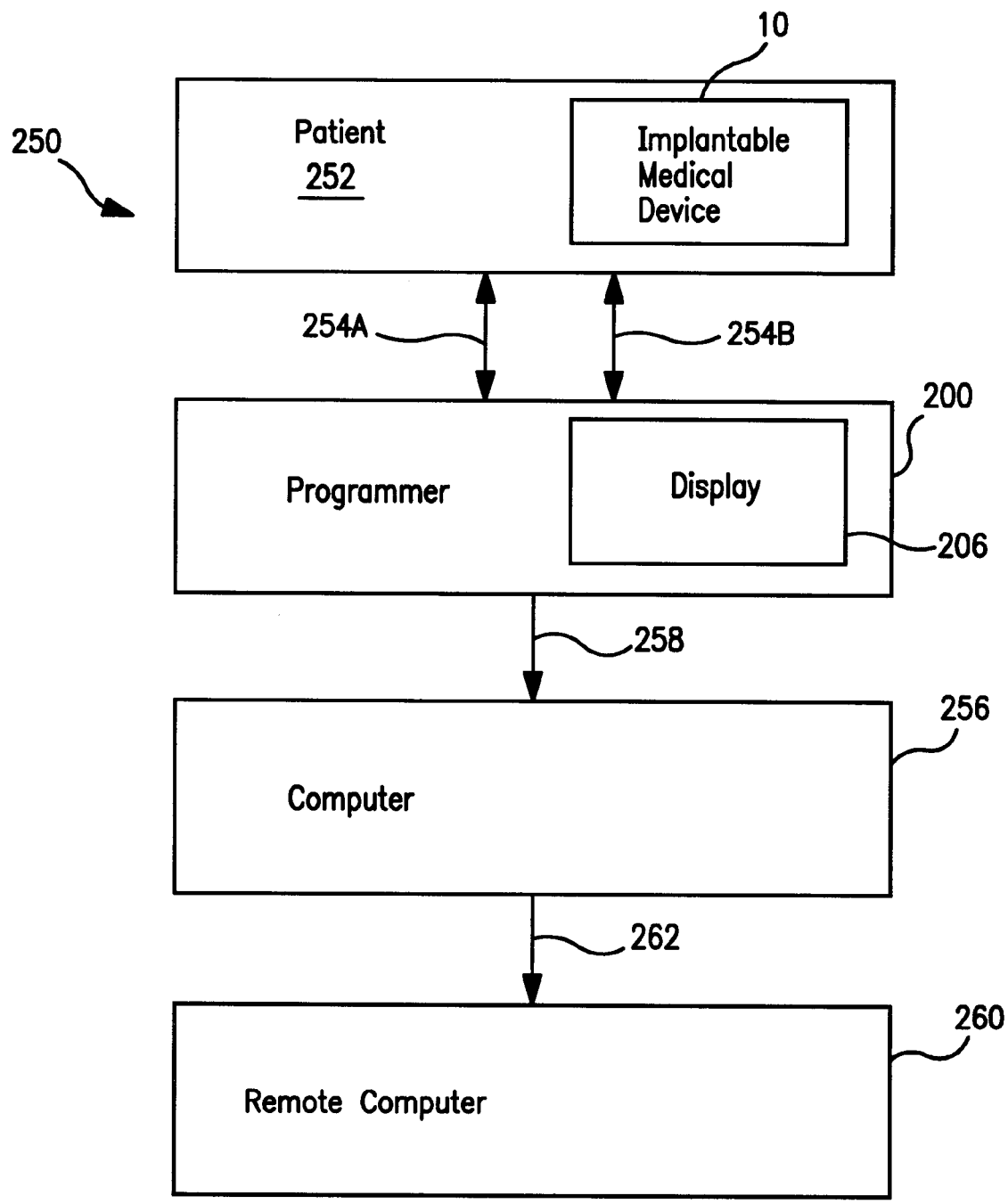
FIG. 7 is a block diagram illustrating a first embodiment showing the interconnections between an implantable medical device and a remote location.

FIG. 7 is a block diagram showing system 250, which includes IMD 10 within patient 252, connections 254a and 254b, programmer 200 having display 206, computer 256, connection 258, remote computer 260, and connection 262.

System 250 can be used at any time when it is necessary or desirous to store information relating to IMD 10 at a remote location or generate a report based on information received from IMD 10 at a remote location.

As shown in FIG. 7, programmer 200 is interconnected to IMD 10 via connections 254a and 254b. Connections 254a and 254b provide radio frequency communication between programmer 206 and IMD 10. A technician or other medical support staff can establish a communication link via connections 254a and 254b and retrieve various information stored within IMD 10. Connection 258 interconnects programmer 200 with computer 256. Connection 258 can be any type of connection which will facilitate the transfer of information between programmer 200 and computer 256. During operation, patient 252, programmer 200, and computer 256 are all located at the same site. Connection 262 interconnects remote computer 260 with computer 256. Remote computer 260 is positioned at a location remote from computer 256, programmer 200, and patient 252. Thus, connection 262 can be any type of connection which will interconnect computer 256 with remote computer 260. For example, connection 262 can be an Internet connection such as a local area network (LAN) connection, a telephone line connection, or a radio frequency connection.

Figure 8:
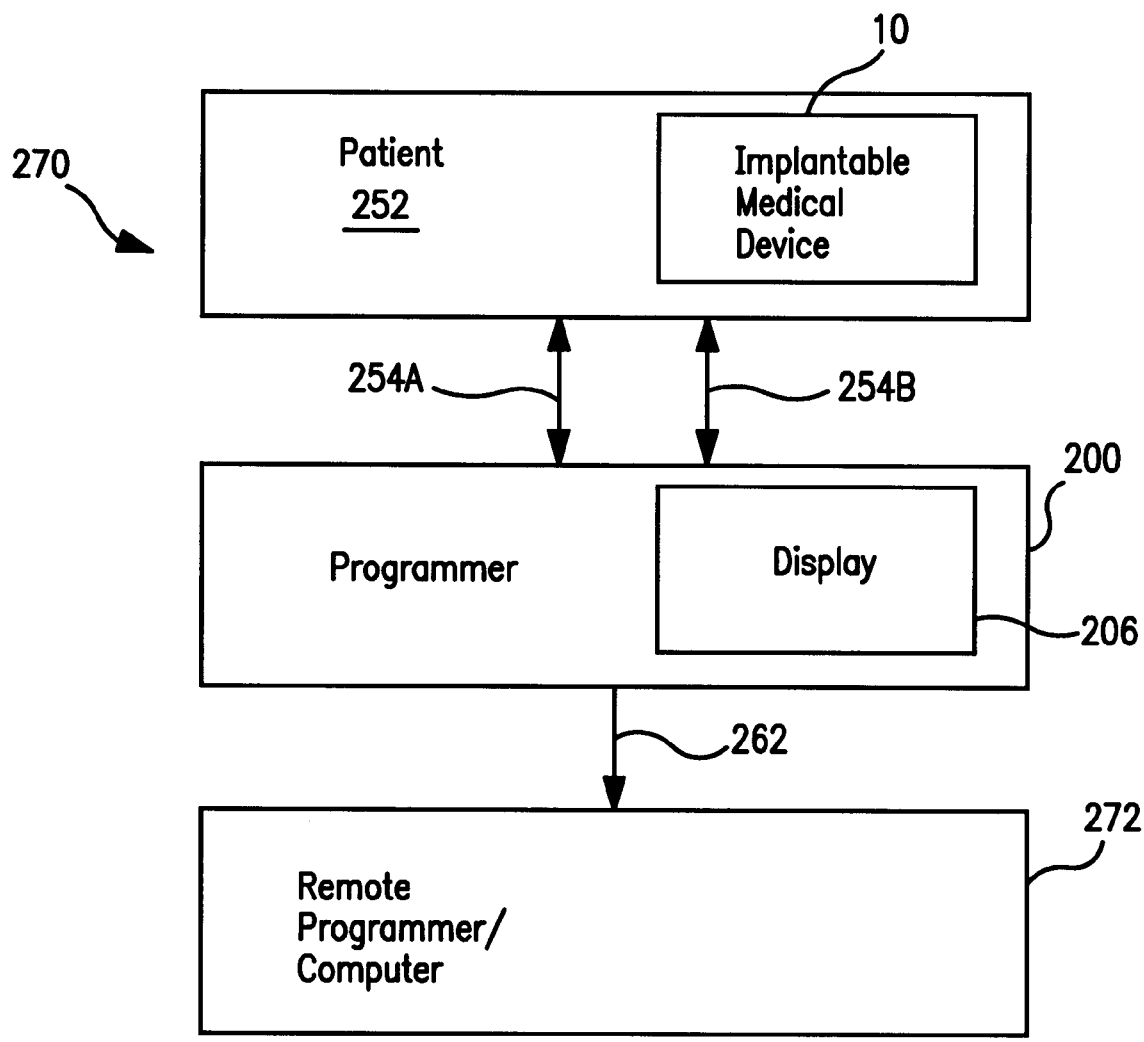
FIG. 8 is a block diagram illustrating a second embodiment showing the interconnections between an implantable medical device and a remote location.

System 270, shown in FIG. 8, is similar to system 250 shown in FIG. 7. However, computer 272 of FIG. 7 has been removed and remote computer 276 of FIG. 7 has been replaced by remote programmer/computer 272. Remote programmer/computer is interconnected to programmer 200 via connection 262, which is identical to connection 262 of FIG. 7. With today's technology, programmers, such as programmer 200, include a microprocessor and has the basic capabilities of a personal computer. Thus, programmer 200 can create a computer file of a digitized signal received from IMD 10 and send the computer file to remote programmer/computer 272 via connection 262. Once again, connection 262 could be LAN connection, a telephone line connection, an Internet connection or a radio frequency connection.

The data stored within IMD 10 can relate to a wide range of information in conjunction with IMD 10 and/or patient 252. For example, specific demographics of patient 252 can be stored within IMD 10, such as the gender, age, and past medical history of patient 252. The information stored within IMD 10 could also include information relating to general procedures of IMD 10, such as constant monitoring of IMD 10 and the results of the pacing and sensing history of IMD 10. Also, IMD 10 can store information relating to a specific test procedure previously or currently completed by IMD 10 or information related to different types of cardiac arrhythmias of patient 252.

All of the information stored within IMD 10 can be transmitted to programmer 200 via connections 254A and 254B in a memory dump procedure which basically transfers the information from IMD 10 to programmer 200 without changing the format of the information. Most implantable medical devices utilize various formats, such as waveform encoding formats, numeric formats, binary formats, and the American Standard Code for Information Interchange (ASCII) format, which is a specification for seven-bit patterns used to represent printable characters and controls (such as a carriage return) used for data communication between microprocessors or computers. ASCII and binary formats are common formats used in the medical device industry.

Since ASCII is a seven-bit code, it can only represent $2^7$ (128) characters. Most computers, however, support eight-bit bytes, which represents $2^8$ (256) characters. So many extended character sets or code pages are usually defined by a specific operating system. Different operating systems include different code pages. Often these code pages are propriety information and are not disseminated. Therefore, it is extremely difficult to understand and manipulate a specific format sent to a system at a remote location utilizing a different code.

In addition, the order and layout of data, as well as any identifiers, often do not adequately match the receiving system which is importing the data. This requires programming language to translate both the data and the order and layout of the data. It is desirous to utilize a self-describing code or language which will have the ability to decipher and understand information relating to IMD 10, regardless of the initial format.

It is also desirous to transfer information relating to IMD 10 via an internet connection to a remote location such that the information can be manipulated, stored, or utilized to generate a report. Most present day prior art computer systems utilize hypertext markup language (HTML) when transferring information via the worldwide web. HTML is a tag-based ASCII language that is used to specify the content and hypertext links to other documents on worldwide web servers on the internet. Browsers can then be used to view the prepared documents and follow links to display other documents. HTML is a structured language which cannot be modified to suit a specific need. Since HTML relies on predefined tags and attributes, there is no control over the structure of data in a HTML document. Thus, while HTML works sufficiently for a text document, it is not compatible with creating a unique format, such as those needed for non-text. Therefore, in relation to systems 250 and 270 shown in FIGS. 7 and 8, a remote programmer or computer cannot properly re-create the information from IMD 10 in a desired format, which then can be stored or presented in a report without the assistance of the present invention.

Figure 9:
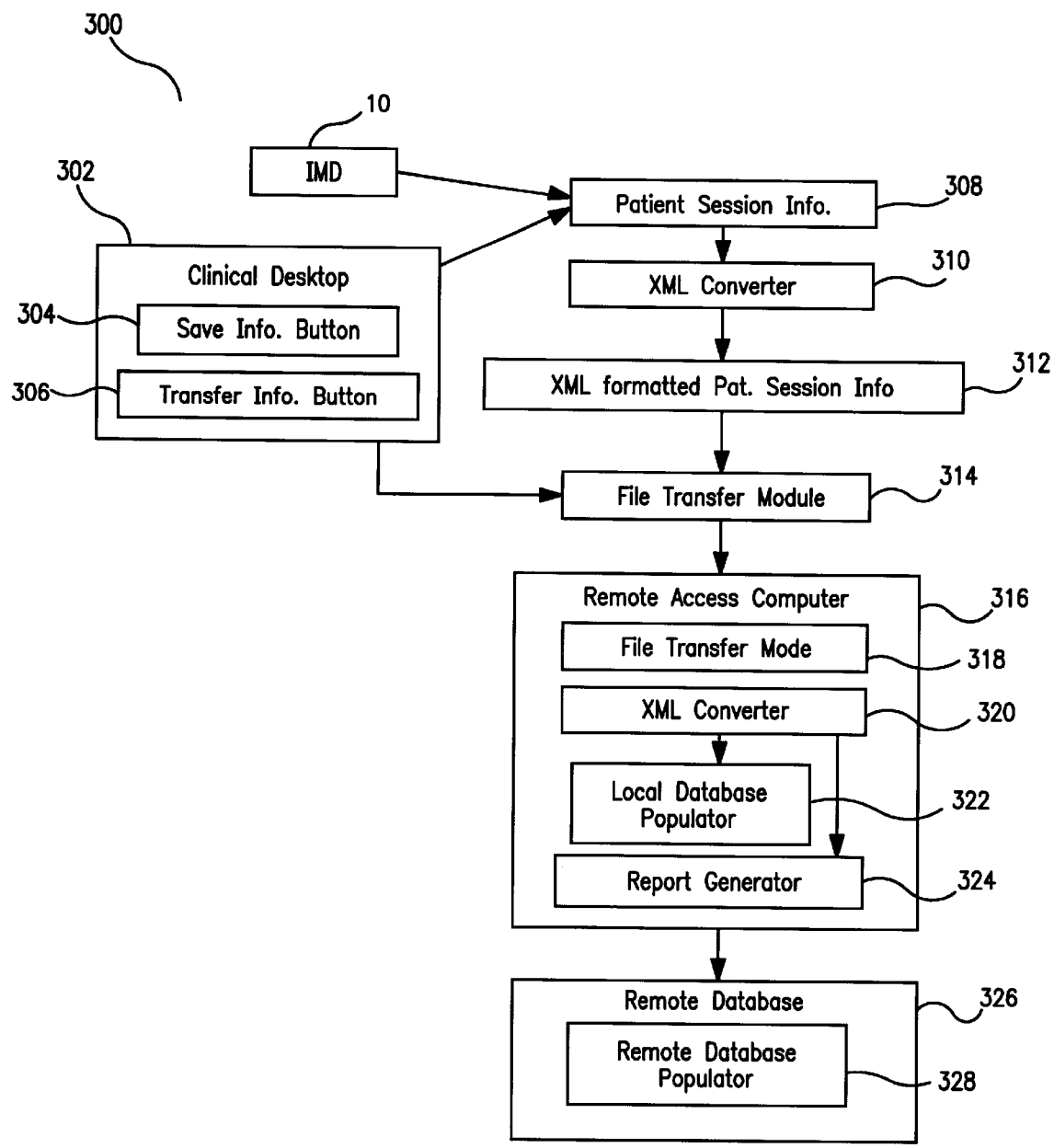
FIG. 9 is a block diagram showing a first embodiment of the present invention.

FIG. 9 is a block diagram showing a first embodiment of the present invention. As shown in FIG. 9, system 300 includes IMD 10, clinical desktop 302 having save information button 304 and transfer information button 306, patient session information 308, extensible markup language (XML) converter 310, XML formatted patient session information 312, file transfer modular 314, remote access computer 316 having file transfer modular 318, XML converter 320, local database populator 322, and report generator 324, and remote database 326 having remote database populator 328.

As shown in FIG. 9, system 300 utilizes XML converter 310. XML arises out of standard generalized markup language (SGML) and HTML standards efforts. XML was formulated by inventor Tim Berners-Lee and the W3 consortium, who also invented the worldwide web. While HTML had predefined tags, XML can be used to define tags as defined. The common mantra of XML is that it separates content from presentation. This is a major difference from HTML. One can use XML to direct a markup language to, in effect, define in-house data handling methods. It allows you to "normalize" varied data input sources to allow complex data handling. XML allows a user to change the definitions of tags as the process evolves. In addition, XML provides embedded structure, which replaces the order and layout of previous mark-up languages, such as SGML and HTML. XML also provides easy validation through the use of data type definition (DTDs) with validating parsers.

Since XML does not rely on predefined tags and attributes, a user has complete control over the structure of data in an XML document. The user can define the tags for components within the document. The user can also add attributes to these tags as necessary. In addition, the user defines how the components fit together. Therefore, XML is a tool which allows various information, such as text, tables, and graphs, to be transmitted over the worldwide web via an internet or other connection to a remote location. The information at the remote location can then be manipulated as necessary, such as through storage of the information or through the generation of a report utilizing the information.

As shown in FIG. 9, a user can initiate save information button 304 on clinical desktop 302 to temporarily save selected portions of information relating either to patient 252 (such as name, gender, height, weight), general information of IMD 10 (such as implant date), or information relating to a specific test procedure of IMD 10. Normally, clinical desktop 302 would be positioned within programmer 200 shown in FIGS. 6, 7, and 8.

The temporarily saved patient information, represented by patient session information 308 is then transferred to XML converter 310. XML converter 310 transfers the patient session information from one or more initial formats, such as an ASCII format, a waveform encoding format, a numeric format, or a binary format, into an XML format. In the embodiment shown in FIG. 9, the XML format would be positioned within programmer 200 shown in FIGS. 6, 7, and 8. XML formatted information 312 can be transferred to remote access computer 316 by a user engaging transfer information button 306. File transfer modular 314 includes a communications module, such as a transmission control protocol (TCP), or more specifically a transmission control protocol/internet protocol (TCP/IP), which provides an error-free connection between two cooperating programs, typically on different computers. A TCP-based communication between programs is often call stream service (or even a reliable stream service), since the receiving program is guaranteed to receive all of the data, with nothing corrupted or duplicated, and in the same sequence as sent. Thus, a feature of the present invention is the ability to transmit information relating to IMD 10 over most communication modules (including wireless communication modules) to a remote location. File transfer modular 314 could be located either in programmer 200 of FIG. 8 or in computer 256 of FIG. 7.

Remote access computer 316 receives the information from file transfer modular 314. File transfer modular 318 (located within remote access computer 316) is similar to file transfer modular 314, while XML converter 320 is similar to XML converter 310. XML 320 converts the selected information from the XML format to a final format. Once the information has been converted to its final format, such as a database usable format or a report format, it can be sent to local database populator 322 or report generator 324 within remote access computer 316, or sent to remote database populator 328 within remote database 326. In most instances, remote database 326 would be a hard drive or a network which remote access computer 316 is operating on. Remote database 326 can be located on the same system as IMD 10, programmer 200, and local computer 256, or can be located on a different system, such as a remote hospital system or a physician's system. One example of remote database 326 is an electronic patient record database.

When the selected information is transferred from either programmer 200 or computer 256 to remote access computer 316 (shown as remote computer 260 in FIG. 7 and as remote programmer/computer 272 in FIG. 8), it can be sent via an Internet connection such as a local area network (LAN), a telephone line connection, or a radio frequency connection. In addition, remote access computer 316 can be a computer operating on the same system as programmer 200 or computer 256 (shown in FIG. 7) or operation on a distinct system. The use of XML format permits this flexibility.

Figure 10:
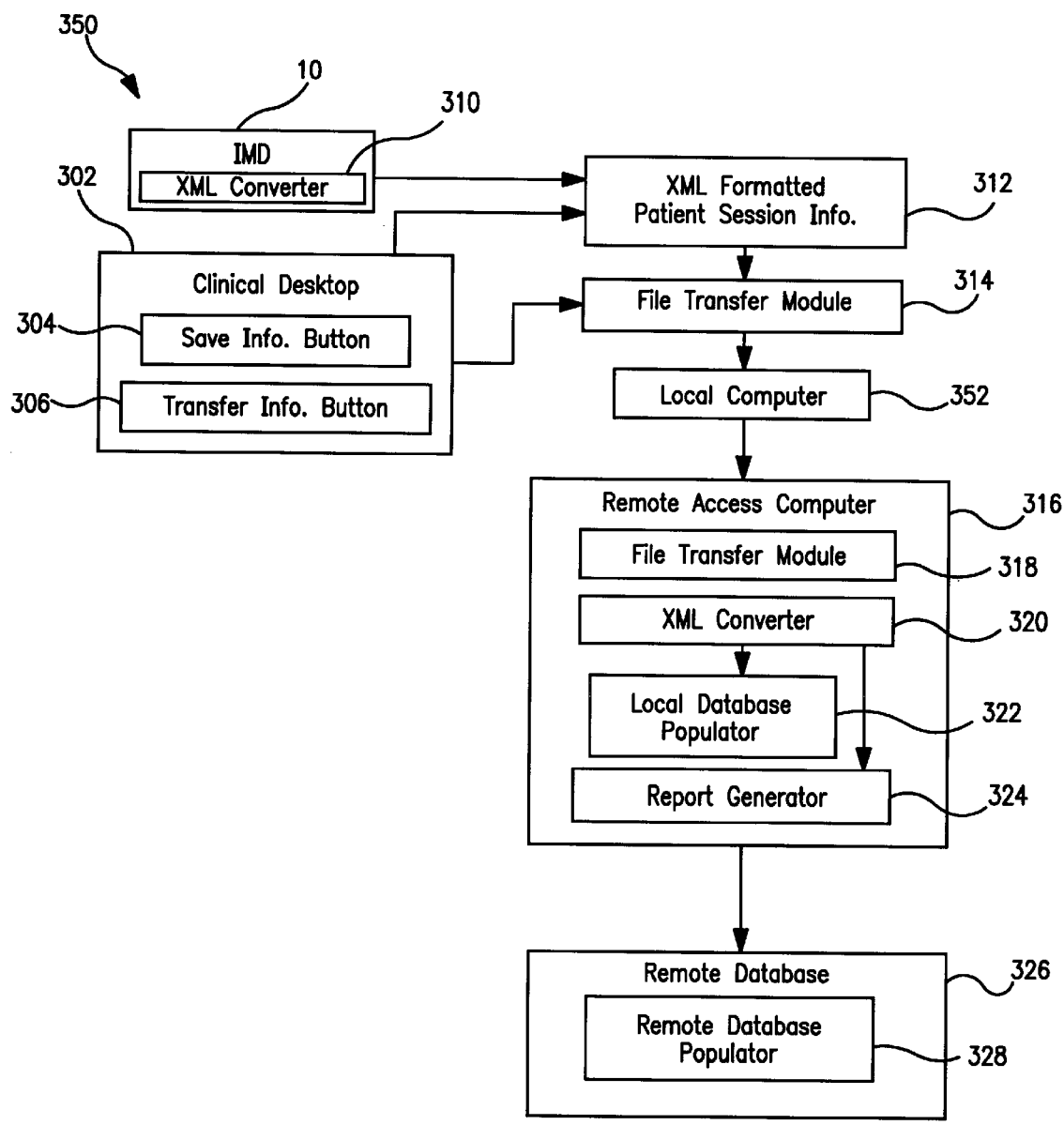
FIG. 10 is a block diagram showing a second embodiment of the present invention.

FIG. 10 is a block diagram showing a second embodiment of the present invention. Several of the elements of FIG. 10 are identical to several of the elements of FIG. 9, and have been labeled as such. System 350, shown in FIG. 10, differs from system 300, shown in FIG. 9, in that XML converter 310 is located within IMD 10, rather than located within programmer 200. Thus, when a user initiates save information button 304, the information has already been transferred into an XML format. XML formatted information 312 can then be transferred to local computer 352 and further transferred to remote access computer 316. The details of system 350 after the conversion of the selected information from the initial format to the XML format are identical of that of system 300, previously described.

The present invention, as shown and described with reference to FIGS. 1–10, transfers a variety of information from an implantable medical device to a remote location in an XML format via one of numerous connections such that the information can be manipulated at the remote end as desired. The present invention transfers selected information from the implantable medical device from an initial format to an XML format. The XML formatted information is then transferred to the remote location, where it is then reformatted from the XML format to its original format. The information can then be stored in a database or can be used to generate a desired report.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A system for transferring information from an implantable medical device to a remote location, the system comprising:
    a first extensible mark-up language converter located within the implantable medical device for converting information relating to the implantable medical device from an initial format to an extensible mark-up language format;
    a programmer for data communication with the implantable medical device, the programmer capable of temporarily saving selected information relating to the implantable medical device within the programmer and capable of transferring the selected information to a remote location; and
    a second extensible mark-up language converter located at the remote location and connected to the programmer for converting the selected information from the extensible mark-up language format to a final format.

2. The system of claim 1 and further comprising:
    a database for receiving the selected information from the second extensible mark-up language converter and for storing the selected information.

3. The system of claim 1 and further comprising:
    a report generator mechanism for receiving the selected information from the second extensible mark-up language converter and for generating a report based upon the selected information.

4. The system of claim 1 wherein the initial format is an American Standard Code for Information Interchange format.

5. The system of claim 1 wherein the programmer further comprises:
    a communications module for providing a connection between the programmer and the remote location.

6. The system of claim 1 and further comprising:
    a communications module located at the remote location for providing a connection between the programmer and the remote location.

7. The system of claim 1 wherein the programmer is capable of transferring the selected information to the remote location via a local area network connection.

8. The system of claim 1 wherein the programmer is capable of transferring the selected information to the remote location via a telephone line connection.

9. The system of claim 1 wherein the programmer is capable of transferring the selected information to the remote location via a radio frequency connection.

10. The system of claim 1 wherein the information relating to the implantable medical device further comprises information relating to demographics of a patient.

11. The system of claim 1 wherein the information relating to the implantable medical device further comprises information relating to a specific test procedure of the implantable medical device.

12. The system of claim 1 wherein the information relating to the implantable medical device further comprises information relating to general procedures of the implantable medical device.

13. The system of claim 1 further comprising a first computer located at the remote location for data communication with the programmer and for receiving the selected information from the programmer.

14. The system of claim 13 further comprising a second computer located at the remote location for data communication with the first computer and for receiving the selected information from the first computer.

15. A system for transferring information from an implantable medical device to a remote location, the system comprising:
    a first extensible mark-up language converter located within the programmer for converting information relating to the implantable medical device from an initial format to an extensible mark-up language format;
    a programmer for data communication with the implantable medical device, the programmer capable of temporarily saving selected information relating to the implantable medical device within the programmer and capable of transferring the selected information to a remote location; and
    a second extensible mark-up language converter located at the remote location and connected to the programmer for converting the selected information from the extensible mark-up language format to a final format.

16. The system of claim 15 further comprising:
    a database for receiving the selected information from the second extensible markup language converter and for storing the selected information.

17. The system of claim 15 further comprising:
    a report generator mechanism for receiving the selected information from the second extensible mark-up language converter and for generating a report based upon the selected information.

18. The system of claim 15 wherein the initial format is an American Standard Code for Information Interchange format.

19. The system of claim 15 wherein the programmer further comprises:
    a communications module for providing a connection between the programmer and the remote location.

20. The system of claim 15 further comprising:
    a communications module located at the remote location for providing a connection between the programmer and the remote location.

21. The system of claim 15 wherein the programmer transfers the selected information to the remote location via a local area network connection.

22. The system of claim 15 wherein the programmer transfers the selected information to the remote location via a telephone line connection.

23. The system of claim 15 wherein the programmer transfers the selected information to the remote location via a radio frequency connection.

24. The system of claim 15 wherein the information relating to the implantable medical device further comprises information relating to demographics of a patient.

25. The system of claim 15 wherein the information relating to the implantable medical device further comprises information relating to a specific test procedure of the implantable medical device.

26. The system of claim 15 wherein the information relating to the implantable medical device further comprises information relating to general procedures of the implantable medical device.

27. The system of claim 15 further comprising a first computer located at the remote location for data communication with the programmer and for receiving the selected information from the programmer.

28. The system of claim 27 further comprising a second computer located at the remote location for data communication with the first computer and for receiving the selected information from the first computer.

29. A system for transferring information from an implantable medical device to a remote location, the system comprising:
- a first extensible mark-up language converter for converting information relating to the implantable medical device from an initial format to an extensible mark-up language format;
- a programmer for data communication with the implantable medical device, the programmer capable of temporarily saving selected information relating to the implantable medical device within the programmer and capable of transferring the selected information to a remote location; and
- a second extensible mark-up language converter located within a computer positioned at the remote location and connected to the programmer for converting the selected information from the extensible mark-up language format to a final format.

30. The system of claim 29 further comprising:
a database for receiving the selected information from the second extensible markup language converter and for storing the selected information.

31. The system of claim 29 further comprising:
a report generator mechanism for receiving the selected information from the second extensible mark-up language converter and for generating a report based upon the selected information.

32. The system of claim 29 wherein the initial format is an American Standard Code for Information Interchange format.

33. The system of claim 29 wherein the programmer further comprises:
a communications module for providing a connection between the programmer and the remote location.

34. The system of claim 29 further comprising:
a communications module located at the remote location for providing a connection between the programmer and the remote location.

35. The system of claim 29 wherein the programmer transfers the selected information to the remote location via a local area network connection.

36. The system of claim 29 wherein the programmer transfers the selected information to the remote location via a telephone line connection.

37. The system of claim 29 wherein the programmer transfers the selected information to the remote location via a radio frequency connection.

38. The system of claim 29 wherein the information relating to the implantable medical device further comprises information relating to demographics of a patient.

39. The system of claim 29 wherein the information relating to the implantable medical device further comprises information relating to a specific test procedure of the implantable medical device.

40. The system of claim 29 wherein the information relating to the implantable medical device further comprises information relating to general procedures of the implantable medical device.

41. The system of claim 29 further comprising a first computer located at the remote location for data communication with the programmer and for receiving the selected information from the programmer.

42. The system of claim 41 further comprising a second computer located at the remote location for data communication with the first computer and for receiving the selected information from the first computer.

43. A system for transferring information from an implantable medical device to a remote location, the system comprising:
- a first extensible mark-up language converter for converting information relating to the implantable medical device from an initial format to an extensible mark-up language format;
- a programmer for data communication with the implantable medical device, the programmer capable of temporarily saving selected information relating to the implantable medical device within the programmer and capable of transferring the selected information to a remote location; and
- a second extensible mark-up language converter located within a second programmer positioned at the remote location having data communications with the programmer for converting the selected information from the extensible mark-up language format to a final format.

44. The system of claim 43 further comprising:
a database for receiving the selected information from the second extensible markup language converter and for storing the selected information.

45. The system of claim 43 further comprising:
a report generator mechanism for receiving the selected information from the second extensible mark-up language converter and for generating a report based upon the selected information.

46. The system of claim 43 wherein the initial format is an American Standard Code for Information Interchange format.

47. The system of claim 43 wherein the programmer further comprises:
a communications module for providing a connection between the programmer and the remote location.

48. The system of claim 43 further comprising:
a communications module located at the remote location for providing a connection between the programmer and the remote location.

49. The system of claim 43 wherein the programmer transfers the selected information to the remote location via a local area network connection.

50. The system of claim 43 wherein the programmer transfers the selected information to the remote location via a telephone line connection.

51. The system of claim 43 wherein the programmer transfers the selected information to the remote location via a radio frequency connection.

52. The system of claim 43 wherein the information relating to the implantable medical device further comprises information relating to demographics of a patient.

53. The system of claim 43 wherein the information relating to the implantable medical device further comprises information relating to a specific test procedure of the implantable medical device.

54. The system of claim 43 wherein the information relating to the implantable medical device further comprises information relating to general procedures of the implantable medical device.

55. The system of claim 43 further comprising a first computer located at the remote location for data communication with the programmer and for receiving the selected information from the programmer.

56. The system of claim 55 further comprising a second computer located at the remote location for data communication with the first computer and for receiving the selected information from the first computer.

* * * * *

UNITED STATES PATENT AND TRADEMARK OFFICE
CERTIFICATE OF CORRECTION

PATENT NO. : 6,250,309 B1  Page 1 of 1
DATED : June 26, 2001
INVENTOR(S) : Krichen et al.

It is certified that error appears in the above-identified patent and that said Letters Patent is hereby corrected as shown below:

<u>Title page,</u>
Item [73], Assignee is missing. Should read -- Medtronic, Inc. Minneapolis, Minnesota --

<u>Column 17, claim 30,</u>
Line 40, "second extensible markup" should read -- second extensible mark-up --

Signed and Sealed this

Fifteenth Day of January, 2002

Attest:

JAMES E. ROGAN
*Attesting Officer*  *Director of the United States Patent and Trademark Office*